United States Patent
Kaulen et al.

(10) Patent No.: US 9,145,518 B2
(45) Date of Patent: Sep. 29, 2015

(54) STABILIZATION OF PYROCARBONIC ACID DIESTERS BY FINELY DIVIDED SOLIDS

(71) Applicant: LANXESS Deutschland GmbH, Cologne (DE)

(72) Inventors: Johannes Kaulen, Odenthal (DE); Erasmus Vogl, Leverkusen (DE)

(73) Assignee: LANXESS DEUTSCHLAND GMBH, Cologne (DE)

( * ) Notice: Subject to any disclaimer, the term of this patent is extended or adjusted under 35 U.S.C. 154(b) by 0 days.

(21) Appl. No.: 14/266,882

(22) Filed: May 1, 2014

(65) Prior Publication Data

US 2014/0234162 A1    Aug. 21, 2014

Related U.S. Application Data

(63) Continuation of application No. 12/299,800, filed as application No. PCT/EP2007/004001 on May 7, 2007, now abandoned.

(30) Foreign Application Priority Data

May 18, 2006    (DE) .......................... 10 2006 023 243

(51) Int. Cl.
| | |
|---|---|
| *A61L 11/00* | (2006.01) |
| *A61L 2/00* | (2006.01) |
| *A61L 2/04* | (2006.01) |
| *A61L 9/00* | (2006.01) |
| *C09K 15/06* | (2006.01) |
| *A23L 2/44* | (2006.01) |
| *A23L 3/3463* | (2006.01) |
| *A23L 3/3499* | (2006.01) |
| *A23L 3/358* | (2006.01) |
| *C07C 68/08* | (2006.01) |
| *C01B 17/69* | (2006.01) |
| *C01B 17/70* | (2006.01) |
| *A23K 3/00* | (2006.01) |
| *A23L 3/34* | (2006.01) |

(52) U.S. Cl.
CPC . *C09K 15/06* (2013.01); *A23L 2/44* (2013.01); *A23L 3/3463* (2013.01); *A23L 3/3499* (2013.01); *A23L 3/358* (2013.01); *C07C 68/08* (2013.01)

(58) Field of Classification Search
USPC .......... 252/407; 423/304, 308, 317, 271, 276; 426/51, 52, 330.3, 590, 597, 599, 654, 426/321; 558/180, 208, 261; 526/8, 11; 422/1
See application file for complete search history.

(56) References Cited

U.S. PATENT DOCUMENTS 5,431,830 A * 7/1995 Erdemir ........................ 508/125

FOREIGN PATENT DOCUMENTS

JP      46-37810    * 11/1971

* cited by examiner

*Primary Examiner* — Bijan Ahvazi

(57) ABSTRACT

Finely divided solids are highly suitable for use as stabilizers for pyrocarbonic acid diesters, it being possible to use the mixtures obtained in this manner for preserving industrial materials and foodstuff.

6 Claims, No Drawings

STABILIZATION OF PYROCARBONIC ACID DIESTERS BY FINELY DIVIDED SOLIDS

This application is a continuation of U.S. patent application Ser. No. 12/299,800, filed Nov. 6, 2008, with the same title, which claims the right of priority under 35 U.S.C. §119 (a)-(d) and 35 U.S.C. §365 of International Application No. PCT/EP2007004001, filed May 7, 2007, which is entitled to the right of priority of German Patent Application No. 10 2006 023 243.7, filed May 18, 2006, the contents of which are hereby incorporated by reference in their entirety.

The present invention relates to the use of finely divided solids as stabilizers for pyrocarbonic acid diesters, to mixtures comprising pyrocarbonic acid diesters and finely divided solids and also to the use of these mixture for preserving industrial materials and foodstuff.

Pyrocarbonic acid diesters are used, inter alia, for preserving foodstuff, as components of antimicrobial reagents, for deactivating enzymes in fermentation processes, or for the synthesis of fine chemicals or polymers. Pyrocarbonic acid diesters are used, in addition, for example as catalysts for the oxidation of amines, or for synthesis, for example in the introduction of protecting groups.

It is known that the stability of pyrocarbonic acid diesters can be relatively low at room temperature, and in particular at elevated temperature. In particular during purification, for example in purification by distillation, or during relatively long storage, decomposition of pyrocarbonic acid diesters can therefore occur. This decomposition can impair the quality and purity of the pyrocarbonic acid diesters. In addition, the decomposition generally proceeds more rapidly the more impurities are present. High purity and stabilization of pyrocarbonic acid diesters are therefore highly desirable.

Methods for improving the thermal stability of pyrocarbonic acid diesters are already known from the prior art. For instance, it is proposed, for example, to stabilize dialkyl pyrocarbonates by adding metal sulphates (cf. JP-A 48-4016). A disadvantage of this method, however, is that these metal sulphates are sparingly to poorly miscible with the dialkyl pyrocarbonates.

In addition, it is known to stabilize dialkyl pyrocarbonates by adding boron compounds (cf. JP-A 46-37810). This, however, has inter alia the disadvantage that these compounds are likewise poorly miscible with the dialkyl pyrocarbonates.

In addition, carbonyl compounds and also heteroanalogous carbonyl compounds have been proposed as additives increasing the storage stability of solutions of dialkyl pyrocarbonates in solvents inert to dialkyl pyrocarbonate (cf. DE-A 3231397). However, stabilizing effects can only be achieved with relatively high percentages of additives.

There was therefore a need for stabilizers suitable for protecting pyrocarbonic acid diesters even more effectively against thermal decomposition.

Surprisingly, it has now been found that pyrocarbonic acid diesters can be stabilized very efficiently by adding certain finely divided solids (insoluble in pyrocarbonic acid diesters) against thermal and/or chemical degradation reactions which may occur, for example, during storage or distillative purification.

Accordingly, the present invention provides the use of at least one finely divided solid as an additive for pyrocarbonic acid diesters for stabilizing them against chemical and/or thermal degradation reactions.

The pyrocarbonic acid diesters are preferably compounds of the general formula (I)

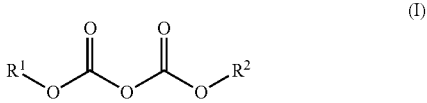

in which
R$^1$ and R$^2$ independently of one another represent straight-chain or branched $C_1$-$C_8$-alkyl, cycloalkyl, $C_2$-$C_8$-alkenyl, $C_2$-$C_8$-alkynyl or benzyl which is in each case optionally mono- or polysubstituted by identical or different substituents from the group consisting of halogen, nitro, cyano, $C_1$-$C_6$-alkoxy, dialkylamino; or represent phenyl which is optionally mono- or polysubstituted by identical or different substituents from the group consisting of halogen, nitro, cyano, alkyl, haloalkyl, alkoxy, haloalkoxy, acyl, acyloxy, alkoxycarbonyl, carboxyl,
preferably
R$^1$ and R$^2$ independently of one another represent straight-chain or branched $C_1$-$C_8$-alkyl or $C_2$-$C_8$-alkenyl or benzyl,
particularly preferably
R$^1$ and R$^2$ independently of one another represent straight-chain or branched $C_1$-$C_5$-alkyl or $C_3$-alkenyl or benzyl,
and very particularly preferably
R$^1$ and R$^2$ independently of one another represent methyl, ethyl, isopropyl, tert-butyl, tert-amyl, allyl or benzyl.

The stabilizer additives to be used according to the invention are finely divided solids which are virtually insoluble in pyrocarbonic acid diesters. The solids are preferably inorganic compounds or mixtures thereof whose solubility in pyrocarbonic acid diesters at room temperature is less than 1 ppm and particularly preferably less than 0.1 ppm.

The particle size, determined by screening, of the finely divided solids to be used according to the invention is preferably in the range of ≤200 μm. Particularly preferably, the particle size, determined by screening, is in the range of ≤80 μm and very particularly preferably in the range of ≤32 μm.

Particles of suitable dimensions can be obtained by grinding the solid to the desired particle size followed by fractional screening using screens having the corresponding mesh sizes of ≤200, 80 or 32 μm. The screens are, for example, analytical screens from Retsch (according to ISO 565/DIN 3310-1).

The finely divided solids to be used according to the invention are preferably metal oxides, metal sulphides and Lewis acids which are present in the solid state of aggregation at room temperature.

Preferred metal oxides are compounds or mixtures thereof of the general formula $M_2O$, $MO$, $M_2O_3$, $MO_2$, $M_2O_5$, $MO_3$, $M_2O_7$, $MO_4$ or double oxides such as, for example, $M_3O_4$, where M is in each case preferably a metal ion or semimetal ion from the group of the first to fourth main group or the transition group or the lanthanoid group of the Periodic Table of the Elements, particularly preferably a metal ion or semimetal ion of the third main group or the transition group or the lanthanoid group of the Periodic Table of the Elements. Very particular preference is given, for example, to $B_2O_3$.

Preferred metal sulphides are compounds of the general formula $M_2S$, $MS$, $M_2S_3$ or $MS_2$, where M is as defined above.

Preferred Lewis acids are, for example, boric acid, metaboric acid, lanthanum triflate, $ZrCl_4$, $HfCl_4$, $TaCl_5$, $WCl_6$, $NbCl_5$ or $YCl_3$.

The general, preferred and particularly preferred solids mentioned can be ground to the desired particle size using instruments usually employed for comminuting, for example in a ball mill or in a mortar.

After comminution, the finely divided solids can be employed directly, or they can be presuspended in a suitable manner. Suitable for suspending are, for example, pyrocarbonic acid diesters, alcohols or water.

The finely divided solids can also be employed immobilized on surfaces. Matrices suitable for this purpose are, for example, activated carbon or silicic carrier materials. Also suitable as matrices for the immobilization are organic polymers, such as, for example, polyethylene, polypropylene, polyesters, polystyrene or polycarbonate.

The finely divided solids mentioned are generally employed in an amount of from 0.01 to 100 000 ppm, preferably in an amount of from 0.1 to 10 000 ppm, particularly preferably in an amount of from 0.1 to 3000 ppm, very particularly preferably in an amount of from 0.1 to 1000 ppm, based on the pyrocarbonic acid diester or its mixture.

By the use according to the invention, it is possible to stabilize pyrocarbonic acid diesters in a general manner against thermal and chemical degradation reactions. Such degradation reactions occur, for example, on storage.

The pyrocarbonic acid diesters stabilized according to the invention are distinguished by improved storage stability. Thus, the pyrocarbonic acid diesters stabilized in this manner can be stored at room temperature over a period of several months without a decomposition of the pyrocarbonic acid diesters being observed.

The present invention furthermore provides mixtures comprising one or more pyrocarbonic acid diesters of the formula (I) shown above and one or more of the finely divided solids described above in a general and a preferred manner in an amount of generally from 0.01 to 100 000 ppm, preferably from 0.1 to 10 000 ppm, particularly preferably from 0.1 to 3000 ppm and very particularly preferably from 0.1 to 1000 ppm, based on the pyrocarbonic acid diester or its mixture.

Very particular preference is given to mixtures comprising dimethyl pyrocarbonate and/or diethyl pyrocarbonate and $B_2O_3$ of a particle size, determined by screening, of ≤32 μm.

The mixtures according to the invention can be stored over a period of several months without a decomposition of the pyrocarbonic acid diesters contained therein occurring.

The mixtures according to the invention are highly suitable for protecting and preserving industrial materials and foodstuff and in particular beverages against attack and/or decomposition by microorganisms, such as, for example, bacteria, fungi or yeasts.

The present invention likewise relates to the use of the mixtures according to the invention for protecting industrial materials and for preserving foodstuff and beverages.

The pyrocarbonic acid diesters stabilized according to the invention are outstandingly suitable, for example, as cold disinfectants for still or carbonated drinks such as soft drinks, vitamin drinks, fruit juice drinks, tea drinks, alcoholic or dealcoholized wine drinks, fruit punches or some beers. Customarily, for this the pyrocarbonic acid diesters are added in amounts between 10 and 250 ppm close in time to packaging the beverages. Admixture to the beverages is performed using special metering pumps. The pyrocarbonic acid diesters act so as to control a number of microorganisms such as fermentative yeasts, moulds or fermentative bacteria. Examples which may be mentioned here are, for instance, *Saccharomyces cervisiae, Mycoderma, Brettanomyces* spp, *Lactobacillus brevis, Lactobacillus buchneri* and many others.

The pyrocarbonic acid diesters stabilized according to the invention are furthermore also suitable for protecting industrial materials against attack and destruction by unwanted microorganisms.

In the present context, industrial materials are to be understood as meaning non-living materials which have been prepared for use in industry. The industrial materials are, for example, adhesives, sizes, paper and board, textiles, leather, wood, timber products, wood composites, paints and plastic articles, cooling lubricants and other materials which can be colonized or destroyed by microorganisms. Furthermore, in the context of the present invention, industrial materials are also to be understood as meaning parts of production plants, for example cooling-water circuits, which may be impaired by the proliferation of microorganisms. Industrial materials which are preferably protected are adhesives, sizes, paper and board, leather, wood, timber products, wood composites, paints, plastic articles, cooling lubricants and heat-transfer liquids.

The pyrocarbonic acid diesters of the general formula (I) stabilized according to the invention are particularly suitable for protecting wood, timber products, wood composites, plastic, cooling lubricants, aqueous and/or solvent-comprising organic or inorganic dispersions and coating systems, such as paints, varnishes or plaster, against colonization by microorganisms.

Microorganisms capable of degrading or changing the industrial materials which may be mentioned are, for example, bacteria, fungi, yeasts, algae and slime organisms. The pyrocarbonic acid diesters stabilized according to the invention preferably act against yeasts, bacteria and fungi.

Mention may be made, for example, of microorganisms of the following genera:

*Acetobacter pasteurianus,*

*Aspergillus,* such as *Aspergillus niger,*

*Candida krusei*

*Chaetomium,* such as *Chaetomium globosum,*

*Escherichia,* such as *Escherichia coli,*

*Penicillium,* such as *Penicillium glaucum,*

*Pseudomonas,* such as *Pseudomonas aeruginosa,*

*Rhodotorula* such as *Rhodotorula rubra*

*Saccharomyces* such as *Saccharomyces cervisiae*

*Staphylococcus,* such as *Staphylococcus aureus.*

Thermal degradation reactions of pyrocarbonic acid diesters also occur, furthermore, in particular in the distillation of pyrocarbonic acid diesters as carried out, for example, in the context of the preparation process for pyrocarbonic acid diesters. By means of the inventive use of finely divided stabilizers it is possible to distil pyrocarbonic acid diesters with lower losses and in higher purity.

Accordingly, the present invention further relates to a process for the distillative purification of pyrocarbonic acid diesters, by adding one or more pyrocarbonic acid diesters of the formula (I) specified above to one or more of the finely divided solids mentioned above as being preferred and particularly preferred, in general in an amount of from 0.01 to 100 000 ppm, preferably in an amount of from 0.1 to 10 000 ppm, in each case based on the pyrocarbonic acid diester or its mixture, and subsequently distilling the mixture at a pressure of from 5 to 100 mbar, preferably from 10 to 50 mbar, and a temperature between 30 and 120° C., preferably between 40 and 90° C. Distillation columns customary in industry are suitable for the distillation.

The yields of pyrocarbonic acid diester in the distillation are usually >99%.

The examples below serve to illustrate the present invention without, however, restricting its subject-matter thereto.

EXAMPLES

Corresponding to the data in Tables 1-3, in each case defined amounts of a defined high-purity pyrocarbonic acid diester and the respective stated solid additives were weighed in a 10 ml round-bottomed flask equipped with a magnetic stirrer. The exact amounts of the additives used in each case are also given in the tables.

The solids were either used directly (coarse) or finely ground beforehand using a mortar (fine). In these experiments, the achieved reduction in particle size was not determined any further. However, for the accurate determination of the particle size, screens having defined mesh sizes (32 μm, 80 μm, 200 μm) were used. Starting with the smallest mesh size, it was thus possible to screen particle sizes as indicated in Table 1 from the stabilizing agent finely comminuted beforehand.

The round-bottomed flask was tightly closed using a septum. In this septum was situated an orifice in which a Teflon tube was attached, which was passed into a vertical silicone-oil-filled 50 ml burette calibrated to 0.1 ml. On the scale of the burette, the amount of the carbon dioxide developing as a result of the decomposition of the pyrocarbonic acid diester could be read off. The flask was promptly lowered into a constant temperature oil bath (stirred at 500 rpm) as specified in Tables 1-3 for the respective experiment. The depth of immersion of the flask was 2.0 cm.

After the respective stated time, in general after 1, 2, 5, 10 and 15 minutes, the gas volume was read off. The gas volume is a measure of the degree of decomposition of the pyrocarbonic acid diester. It thus inversely reflects the degree of stabilization by the additives tested.

The results are shown in the appended tables. High-purity pyrocarbonic acid diester, in the observed time, released little carbon dioxide, but even contact with small amounts of silica gel drastically accelerated decomposition. The more finely divided the stabilizer, the higher its stabilizing effect.

TABLE 1

Diethyl dicarbonate, 5000 ppm addition of solid stabilizer

| | | | | | | |
|---|---|---|---|---|---|---|
| Temperature [° C.] | 130 | 130 | 130 | 130 | 130 | 130 |
| Diethyl dicarbonate quantity [g] | 1 | 1 | 1 | 1 | 1 | 1 |
| Addition | without | silica gel | silica gel | silica gel | silica gel | silica gel |
| Quantity [mg] | | 10 | 10 | 10 | 10 | 10 |
| Addition solid | without | Without | $B_2O_3$ | $B_2O_3$ | $B_2O_3$ | $B_2O_3$ |
| Quantity [mg] | | | 5 | 5 | 5 | 5 |
| Particle size [μm] | | | <32 μm | 32-80 μm | 80-200 μm | >1000 μm |
| Evolution of gas [ml] | | | | | | |
| Minutes 1 | 0.5 | 2.5 | 0.9 | 1.9 | 2.4 | 1.7 |
| Minutes 2 | 1.0 | 7.2 | 2.0 | 3.8 | 4.3 | 5.1 |
| Minutes 5 | 1.2 | 28.9 | 3.1 | 6.0 | 7.4 | 11.1 |
| Minutes 10 | 1.3 | 46.3 | 4.9 | 8.1 | 10.0 | 22.3 |
| Minutes 15 | 1.3 | 50.0 | 6.9 | 10.1 | 12.1 | 32.0 |

TABLE 2

Dimethyl dicarbonate, 6670 ppm addition of solid stabilizer

| | | | | | | |
|---|---|---|---|---|---|---|
| Temperature [° C.] | 100 | 100 | 100 | 100 | 100 | 100 |
| Dimethyl dicarbonate quantity [g] | 3 | 3 | 3 | 3 | 3 | 3 |
| Addition | without | silica gel | silica gel | silica gel | silica gel | silica gel |
| Quantity [mg] | | 10 | 10 | 10 | 10 | 10 |
| Addition solid | without | Without | Boric acid coarse | Boric acid fine | $B_2O_3$ coarse | $B_2O_3$ fine |
| Quantity [mg] | | | 20 | 20 | 20 | 20 |
| Evolution of gas [ml] | | | | | | |
| Minutes 1 | 0.1 | 1.0 | 0.9 | 0.4 | 0.8 | 0.7 |
| Minutes 2 | 0.2 | 3.4 | 3.3 | 1.8 | 2.8 | 2.2 |
| Minutes 5 | 0.6 | 20.3 | 7.7 | 3.9 | 7.3 | 4.9 |
| Minutes 10 | 0.8 | 46.1 | 10.0 | 5.1 | 12.7 | 6.4 |
| Minutes 15 | 1.3 | 50.0 | 10.9 | 6.1 | 15.8 | 7.2 |

TABLE 3

| Dimethyl dicarbonate, 1670 ppm addition of solid stabilizer | | | | |
|---|---|---|---|---|
| Temperature [° C.] | 100 | 100 | 100 | 100 |
| Dimethyl dicarbonate quantity [g] | 3 | 3 | 3 | 3 |
| Addition | without | silica gel | silica gel | silica gel |
| Quantity [mg] | | 10 | 10 | 10 |
| Addition solid | without | without | $B_2O_3$ coarse | $B_2O_3$ fine |
| Quantity [mg] | | | 5 | 5 |
| Evolution of gas [ml] | | | | |
| Minutes 1 | 0.1 | 1.0 | 0.4 | 0.4 |
| Minutes 2 | 0.2 | 3.4 | 2.1 | 1.8 |
| Minutes 5 | 0.6 | 20.3 | 9.8 | 6.1 |
| Minutes 10 | 0.8 | 46.1 | 22.6 | 12.6 |
| Minutes 15 | 1.3 | 50.0 | 32.9 | 16.6 |

What is claimed is:

1. A method for extending the preservation of a foodstuff or beverage treated with pyrocarbonates, the method comprising:
   contacting the foodstuff or beverage with:
   a) one or more dialkyl pyrocarbonates selected from the group consisting of dimethyl pyrocarbonate, diethyl pyrocarbonate, and mixtures thereof; and
   b) boron trioxide in an amount of 0.01 to 100,000 ppm, based on the one or more dialkyl pyrocarbonates, wherein the boron trioxide has a particle size of ≤32 μm,
   to reduce chemical and/or thermal degradation reactions of the dialkyl pyrocarbonates and extend the preservative ability of the dialkyl pyrocarbonates.

2. The process according to claim 1, further comprising mixing the one or more dialkyl pyrocarbonates and the boron trioxide prior to contacting the foodstuff or beverage.

3. The process according to claim 1, wherein the contacting comprises contacting the foodstuff or beverage individually with the one or more dialkyl pyrocarbonates and the boron trioxide.

4. The process according to claim 1, wherein the amount of boron trioxide is 0.01 to 1000 ppm.

5. The process according to claim 1, wherein the amount of boron trioxide is 0.1 to 1000 ppm.

6. The process according to claim 1, wherein the size of the boron trioxide is determined by screening.

* * * * *